(12) United States Patent
Okutsu et al.

(10) Patent No.: US 6,207,845 B1
(45) Date of Patent: Mar. 27, 2001

(54) ALUMINUM COMPOUNDS AND USE THEREOF

(75) Inventors: Munehisa Okutsu; Tomohito Kitsuki; Katsumi Kita, all of Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/403,765

(22) PCT Filed: Jan. 22, 1998

(86) PCT No.: PCT/JP98/00238

§ 371 Date: Nov. 1, 1999

§ 102(e) Date: Nov. 1, 1999

(87) PCT Pub. No.: WO98/50389

PCT Pub. Date: Nov. 12, 1998

(30) Foreign Application Priority Data

May 1, 1997 (JP) .................................................. 9-113855
Sep. 12, 1997 (JP) .................................................. 9-243156

(51) Int. Cl.[7] ............................. C07F 5/06; B01J 31/12; C07D 301/27
(52) U.S. Cl. ........................ 556/177; 556/182; 556/186; 568/688; 568/697; 549/516
(58) Field of Search .................................. 556/177, 182, 556/186; 568/588, 697; 549/516

(56) References Cited

U.S. PATENT DOCUMENTS 3,267,154 * 8/1966 Hokama .............................. 260/619

* cited by examiner

Primary Examiner—Porfirio Nazario-Gonzalez
(74) Attorney, Agent, or Firm—Oblon, Spivak, McClelland, Maier & Neustadt, P.C.

(57) ABSTRACT

An aluminum compounds represented by the following general formula (1):

$$Al(R^1-SO_3)_l(R^2)_m(R^3)_n \qquad (1)$$

wherein $R^1$ is a hydrocarbon group which may be substituted, $R^2$ is a hydrocarbon group which may be substituted, an aliphatic hydrocarbonoxy group which may be substituted, or a halogen atom, $R^3$ is an aromatic hydrocarbonoxy group which may be substituted, and l, m and n are independently a number of 0 to 3, with the proviso that l+m+n equals 3, and l is not 0, an acid catalyst comprising the aluminum compound, and a process for producing an ester, acetal, ketal, ether or alkyl glycoside making use of the catalyst.

The catalyst is suitable for use in a variety of acid-catalyzed reactions of alcohols, i.e., reactions with carbonyl compounds, such as esterification, transesterification, acetalization and ketalization, etherification, ring-opening reactions of epoxy compounds, etc. in addition to the above-described respective reactions, is not deactivated by alcoholysis, has a sufficient activity, can easily control a reaction catalyzed thereby and scarcely causes side reactions. Consequently, the use of the catalyst permits the production of the intended product at a high yield from starting materials used in an almost equimolar proportion.

14 Claims, 1 Drawing Sheet

ALUMINUM COMPOUNDS AND USE THEREOF

TECHNICAL FIELD

The present invention relates to novel aluminum compounds useful as acid catalysts and a production process of an ester, acetal, ketal, ether or alkyl glycoside using such a compound as an acid catalyst.

BACKGROUND ART

As production processes of glycidyl ethers, there have heretofore been mainly known a single-stage process in which an alcohol and an α-epihalohydrin are reacted with each other by an alkali in the presence of a phase-transfer catalyst such as a quaternary ammonium salt, and a two-stage process in which an alcohol and an α-epihalohydrin are reacted with each other in the presence of an acid catalyst to form a halohydrin ether, and the halohydrin ether is then cyclized by an alkali. However, in the single-stage process, it is necessary to use the α-epihalohydrin in excess in order to avoid further addition of the alcohol to the formed glycidyl ether. In the two-stage process, the conversion of the alcohol becomes low when the acid catalyst is a BrØnsted acid such as sulfuric acid, while a further addition reaction of the α-epihalohydrin to the formed halohydrin ether tends to occur when a high-active Lewis acid catalyst such as boron trifluoride or tin tetrachloride is used. In order to avoid this reaction, it is necessary to use the alcohol in excess to the α-epihalohydrin. Besides, the use of a metal chloride such as aluminum chloride, tin chloride or iron chloride as the Lewis acid catalyst also involves problems that the catalyst is deactivated by alcoholysis, and that free chlorine generated reacts with the α-epihalohydrin. Further, in order to efficiently conduct the ring closure of the halohydrin ether by the alkali, there is also a problem that a hydrophilic solvent and a phase-transfer catalyst must be used.

Processes for producing a dialkyl glyceryl ether include a process in which an alcohol is reacted with an α-epihalohydrin in the presence of an alkali, and a process in which glycerol is reacted with an alkyl halide in the presence of an alkali. However, both processes require to use the alcohol or alkyl halide in great excess and involve a problem that it is extremely difficult to introduce 2 different alkyl groups at the same time. When an alcohol is reacted with glycidyl ether in the presence of an alkali or acid catalyst, a dialkyl glycidyl ether can be obtained with the alkyl groups freely selected. However, in the case where the alkali is used, it is necessary to use the alcohol in excess in order to avoid an additional reaction of the formed product. There is also a problem that glycidyl ether is partially hydrolyzed. In the case where the acid is used on the other hand, there is a problem that glycidyl ether undergoes polymerization.

Production processes of an alkyl glycoside include a process in which a sugar is reacted directly with a higher alcohol in the presence of an acid catalyst (U.S. Pat. No. 3,839,318 etc.). However, this process involves a problem that when the sugar is caused to coexist with water and the acid catalyst, the sugar undergoes condensation to form a by-product, so that the yield is lowered, and the deterioration of hue is incurred. When the sugar is a monosaccharide in particular, the alkyl glycoside formed may condense with the monosaccharide in some cases, so that the yield of the alkyl glycoside is markedly lowered. As a process for preventing such condensation of the sugar itself, or of the alkyl glycoside formed with the sugar to obtain the intended alkyl glycoside at a high yield, a process in which a higher alcohol is used in excess to the sugar has been known (Japanese Patent Application Laid-Open No. 5199/1984 etc.). However, this process requires to remove excessive unreacted alcohol. In the course of this operation, deterioration of smell and the like may occur in some cases, and there is an economical problem that the productivity is markedly lowered. There is also a problem that the degree of condensation of the sugar is rapidly raised as the conversion of the sugar becomes high, and the concentration of the alkyl glycoside in the system is raised.

Accordingly, it is an object of the present invention to provide an acid catalyst which is suitable for use in a variety of acid-catalyzed reactions of alcohols, i.e., reactions with carbonyl compounds, such as esterification, transesterification, acetalization and ketalization, etherification, ring-opening reactions of epoxy compounds, etc. in addition to the above-described respective reactions, is not deactivated by alcoholysis, has a sufficient activity, can easily control a reaction catalyzed thereby and scarcely causes side reactions.

Another object of the present invention is to provide a production process of an ester, acetal, ketal, ether or alkyl glycoside making use of the above catalyst, by which the intended product can be produced at a high yield even when starting materials are used in an almost equimolar proportion.

DISCLOSURE OF THE INVENTION

The present inventors have carried out an extensive investigation with a view toward solving the above-described problems. As a result, it has been found that novel aluminum compounds represented by the general formula (1), which will be described subsequently, are excellent acid catalysts satisfying the above requirements, thus leading to completion of the present invention.

According to the present invention, there is thus provided an aluminum compound represented by the following general formula (1):

$$Al(R^1\text{—}SO_3)_l(R^2)_m(R^3)_n \qquad (1)$$

wherein $R^1$ is a hydrocarbon group which may be substituted, $R^2$ is a hydrocarbon group which may be substituted, an aliphatic hydrocarbonoxy group which may be substituted, or a halogen atom, $R^3$ is an aromatic hydrocarbonoxy group which may be substituted, and l, m and n are independently a number of 0 to 3, with the proviso that l+m+n equals 3, and l is not 0.

According to the present invention, there is also provided an acid catalyst comprising the aluminum compound described above.

According to the present invention, there is further provided a process for producing an ester, acetal, ketal, ether or alkyl glycoside, which comprises reacting an alcohol with a carbonyl compound, alcohol, olefin, epoxy compound or sugar in the presence of the above acid catalyst, or (A) an aluminum alkoxide and (B) a phenol and/or a sulfonic acid.

BEST MODE FOR CARRYING OUT THE INVENTION

Figure 1:
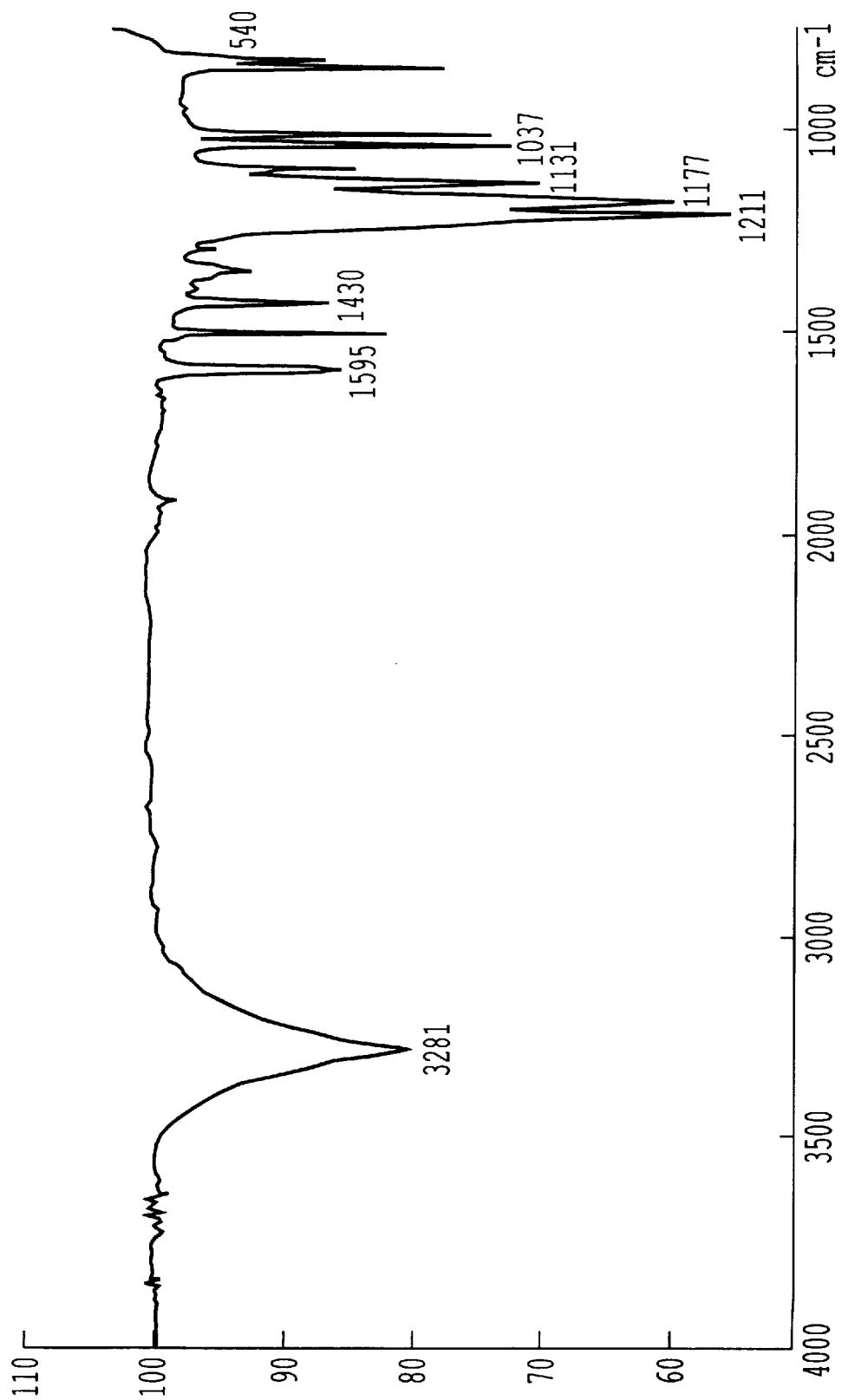
FIG. 1 illustrates an IR spectrum of a compound (a) according to the present invention.

Examples of the hydrocarbon group represented by $R^1$, which may be substituted, include alkyl groups which may be substituted by at least one hydroxyl group, alkoxyl group or halogen atom; alkenyl groups which may be substituted by at least one hydroxyl group, alkoxyl group or halogen atom; and aryl groups which may be substituted by at least one alkyl, hydroxyl group, alkoxyl group or halogen atom. The alkyl groups which may be substituted include linear or branched alkyl groups having 1 to 36 carbon atoms, and specific examples thereof include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, 2-ethylhexyl and 3,5-dimethylhexyl groups. The alkenyl groups which may be substituted include linear or branched alkenyl groups having 2 to 36 carbon atoms, and specific examples thereof include vinyl, propenyl, oleyl and linolyl groups. The aryl groups which may be substituted include phenyl and naphthyl groups. Examples of the alkoxyl group which may be substituted on these alkyl, alkenyl and aryl groups include linear or branched alkoxyl groups having 1 to 36 carbon atoms, and specific examples thereof include methoxyl, ethoxyl, propoxyl, isopropoxyl, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, eicosyloxy, 2-ethylhexyloxy and 3,5-dimethylhexyloxy groups. Examples of the halogen atoms which may be substituted on the alkyl, alkenyl and aryl groups include chlorine, bromine, fluorine and iodine atoms. Examples of the alkyl group which may be substituted on the aryl group include the same linear or branched alkyl groups having 1 to 36 carbon atoms as described above.

Of these groups which represent $R^1$, the alkyl, alkenyl, phenyl and naphthyl groups which may be substituted, particularly, the alkyl, phenyl and naphthyl groups which may be substituted are preferred. Of these, particularly preferred are methyl and trifluoromethyl groups as the alkyl groups which may be substituted; phenyl, chlorophenyl, methylphenyl, ethylphenyl, propylphenyl, butylphenyl, dodecylphenyl, methoxyphenyl, ethoxyphenyl, propoxyphenyl, butoxyphenyl and hydroxyphenyl groups as the phenyl group which may be substituted; and a hydroxynaphthyl group as the naphthyl group which may be substituted. $R^1$ is most preferably a hydroxyphenyl group.

In the general formula (1), examples of the hydrocarbon group represented by $R^2$, which may be substituted, include the same groups as those mentioned in $R^1$, and besides those groups having a polyoxyalkylene group as a substituent group. Examples of the aliphatic hydrocarbonoxy group represented by $R^2$, which may be substituted, include alkoxyl groups which may be substituted by at least one hydroxyl group, alkoxyl group, polyoxyalkylene group or halogen atom; and alkenyloxy groups which may be substituted by at least one hydroxyl group, alkoxyl group, polyoxyalkylene group or halogen atom. Here, the alkoxyl groups which may be substituted, and the alkoxyl groups and halogen atoms as substituents include those mentioned above. The alkenyloxy groups which may be substituted include linear or branched alkenyloxy groups having 2 to 36 carbon atoms, and specific examples thereof include propenyloxy, oleyloxy and linolyloxy groups. Of these aliphatic hydrocarbonoxy groups which may be substituted, alkoxyl and alkenyloxy groups, particularly, alkoxyl groups are preferred. $R^2$ may be a halogen atom. In this case, the halogen atom is preferably a chlorine or bromine atom. $R^2$ is particularly preferably an isopropoxyl group.

In the general formula (1), examples of the aromatic hydrocarbonoxy group represented by $R^3$, which may be substituted, include aryloxy groups which may be substituted by at least one alkyl group, hydroxyl group, alkoxyl group or halogen atom, and particularly preferable specific examples thereof include phenoxyl, hydroxyphenoxyl, chlorophenoxyl, dichlorophenoxyl, trichlorophenoxyl and naphthoxyl groups.

Specific examples of the aluminum compounds (1) include the following compounds:

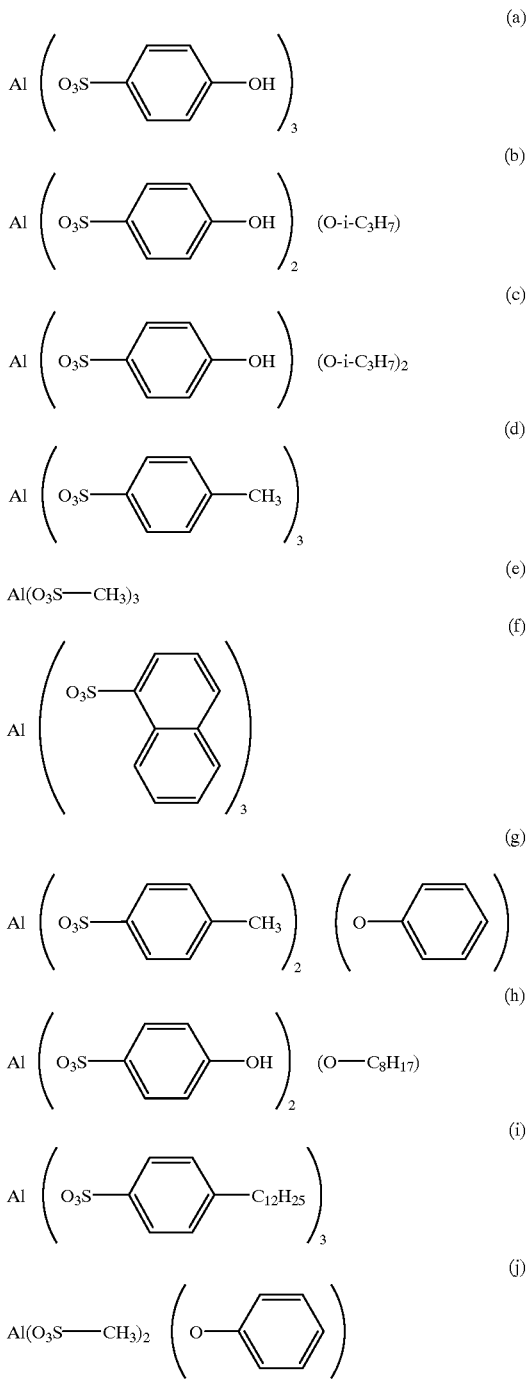

The aluminum compounds (1) are prepared by reacting, for example, a trialkylaluminum, trialkoxyaluminum or aluminum trihalide (halogen: chlorine or bromine) with a sulfonic acid to substitute the sulfonic acid for a part or the whole of the alkyl groups in the trialkylaluminum, the alkoxyl groups in the trialkoxyaluminum or halogeno-groups in the aluminum trihalide, and then substituting a proper alcohol or phenol for the residual alkyl groups, alkoxyl groups or halogeno-groups. The substitution reaction with the sulfonic acid and the substitution reaction with the alcohol or phenol are conducted by, for example, heating the reactants in a solvent such as a hydrocarbon or alcohol.

Of the aluminum compounds (1) according to the present invention, those synthesized from aluminum isopropoxide and p-phenolsulfonic acid, i.e., the above-described compounds (a), (b) and (c), are particularly preferred.

The aluminum compounds (1) are useful as acid catalysts, particularly, as acid catalysts for various reactions making use of an alcohol as a starting material.

When the aluminum compound (1) is used as an acid catalyst in a reaction of an alcohol with a carbonyl compound, alcohol, olefin, epoxy compound or sugar, an ester, acetal, ketal, ether or alkyl glycoside is obtained at a high yield without deactivating the catalyst by alcoholysis. In this reaction, side reactions can also be reduced. The aluminum compounds (1) are particularly useful in a reaction of an alcohol with an epoxy compound to obtain an ether (a ring-opening reaction of the epoxy compound) among others. More specifically, in this reaction, deactivation of the catalyst by alcoholysis, which is apt to occur upon the use of a metal chloride such as iron chloride, does not occur, and side reactions such as polymerization of the epoxy compound are reduced.

No particular limitation is imposed on the alcohol used as a starting material in these reactions. However, examples thereof include those represented by the following general formula (2):

$$R^4—(OA^1)_p—OH \qquad (2)$$

wherein $R^4$ is a saturated or unsaturated, linear or branched hydrocarbon group having 1 to 36 carbon atoms in total, $A^1$ is an alkylene group having 2 to 4 carbon atoms, and p is a number of 0 to 100. Specific examples of the alcohols include aliphatic saturated alcohols such as methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, 2-ethylhexanol and 3,5-dimethyl-hexanol; and besides aliphatic unsaturated alcohols such as oleyl alcohol and linolyl alcohol, and alkylene oxide adducts thereof. As such alkylene oxide adducts, ethylene oxide adducts (in the general formula (2), $A^1$ being ethylene) are preferred. The number (p in the general formula (2)) of moles added is preferably 0 to 20. However, as the alcohols, those (in the general formula (2), p being 0) added with no alkylene oxide are preferred.

Examples of the epoxy compound used as a starting material in the reaction of the alcohol with the epoxy compound include α-epihalohydrins such as α-epichlorohydrin, α-epibromohydrin and α-epiiodehydrin, and 1,2-epoxy compounds represented by the following general formula (3):

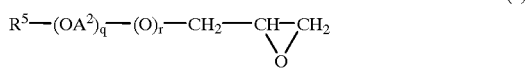

(3)

wherein $R^5$ is a saturated or unsaturated, linear or branched hydrocarbon group having 1 to 24 carbon atoms, which may be substituted, $A^2$ is an alkylene group having 2 to 4 carbon atoms, q is a number of 0 to 100, and r is 0 or 1.

In the general formula (3), examples of the saturated or unsaturated, linear or branched hydrocarbon group having 1 to 24 carbon atoms represented by $R^5$, which may be substituted, include alkyl groups such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, 2-ethylhexyl and 3,5-dimethylhexyl groups, and besides alkenyl groups such as oleyl and linolyl groups. No particular limitation is imposed on the substituents that these groups may have. However, examples thereof include halogen atoms such as fluorine and chlorine atoms, a hydroxyl group, and alkoxyl groups.

In the general formula (3), the alkylene group having 2 to 4 carbon atoms represented by $A^2$ is preferably an ethylene group. The number of 0 to 100 represented by q is preferably 0 to 20, particularly 0. More specifically, the 1,2-epoxy compound (3) used is preferably that added with no alkylene oxide.

In the general formula (3), r represents 0 or 1, with 1 being preferred. More specifically, the 1,2-epoxy compound (3) used is an a-olefin oxide (r=0) or a glycidyl ether (r=1), with the glycidyl ether being preferred.

When an α-epihalohydrin is used as the epoxy compound, a halohydrin ether is provided. When an alkali is added to the reaction mixture thereof without removing the catalyst, thereby conducting dehydrohalogenation, a ring-closing reaction is allowed to successfully progress, thereby obtaining a glycidyl ether. The alcohol used in this case is preferably that represented by the general formula (2), in which the number of carbon atoms in $R^4$ is 5 to 8. Examples of the alkali used in the ring-closing reaction include alkali metal hydroxides such as sodium hydroxide and potassium hydroxide, and alkaline earth metal hydroxides such as calcium hydroxide and barium hydroxide, with sodium hydroxide and potassium hydroxide being particularly preferred. In the ring-closing reaction of the halohydrin ether, it is preferable to use the alkali in an amount of 1.0 to 4.0 mol, particularly 1.0 to 2.5 mol, per mol of the alcohol charged. The alkali is preferably added in the form of, for example, a 10 to 50% aqueous solution. The reaction is preferably performed at a temperature of 40 to 110° C. for several hours. The glycidyl ether obtained in accordance with the present invention can be further converted into a monoalkyl glyceryl ether by hydrolyzing it in accordance with a method known per se in the art.

When the compound (3) is used as the epoxy compound, an ether represented by the following general formula (4):

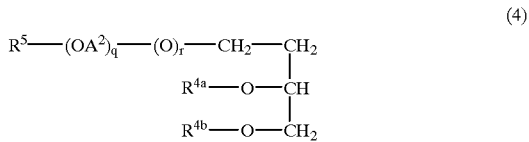

(4)

wherein $R^5$, $A^2$, q and r have the same meanings as defined above, and one of $R^{4a}$ and $R^{4b}$ is a hydrogen atom and the other is $R^4—(OA^1)_p—$ ($R^4$, $A^1$ and p having the same meanings as defined above), is provided.

The sugar used as a starting material in the reaction of the alcohol with the sugar may be any of monosaccharides, oligosaccharides and polysaccharides. Examples of the monosaccharides include aldoses such as allose, altrose, glucose, mannose, gulose, idose, galactose, talose, ribose, arabinose, xylose and lyxose. Examples of the oligosaccharides include maltose, lactose, sucrose and maltotriose. Examples of the polysaccharides include hemicellulose, inulin, dextrin, dextran, xylan, starch and hydrolyzed starch. Of these, monosaccharide having at most 6 carbon atoms are preferred, with glucose being particularly preferred. The sugar may be hydrous or anhydrous. However, an anhydrous solid sugar is preferably used.

In the present invention, the alkyl glycoside obtained by the reaction of the alcohol and the sugar is preferably an alkyl glycoside which has a linear or branched alkyl group having 8 to 14 carbon atom, and a condensation degree of sugar skeletons of 1 to 1.4. Such an alkyl glycoside is prepared from a linear or branched alcohol having 8 to 14 carbon atoms and hydrous or anhydrous glucose.

The reaction of the alcohol with the carbonyl compound, alcohol, olefin, epoxy compound or sugar may be conducted in the same manner as in the ordinary esterification, acetalization, ketalization or etherification except that the aluminum compound (1) is used as an acid catalyst. For example, the reaction of the alcohol with the epoxy compound may be performed at a temperature of 10 to 120° C., preferably 70 to 110° C. for 1 to 5 hours by using the epoxy compound and the aluminum compound (1) in amounts of 0.5 to 1.5 mol, preferably 1.0 to 1.2 mol and 0.001 to 0.1 mol, preferably 0.01 to 0.05 mol, respectively, per mol of the alcohol. The reaction of the alcohol with the sugar may be performed at a temperature of 90 to 130° C., preferably 90 to 120° C. under a pressure of 5 to 100 mmHg, particularly 20 to 60 mmHg by using the alcohol and the aluminum compound (1) in amounts of 1 to 10 mol, particularly 2 to 4 mol and 0.001 to 0.1 mol, particularly 0.01 to 0.1 mol, respectively, per mol of the sugar.

All the above-described various reactions making use of the alcohols as starting materials may also be performed by using (A) an aluminum alkoxide and (B) a phenol and/or a sulfonic acid in place of the acid catalyst comprising the aluminum compound (1) and in the presence of these compounds. Even in this case, the same good results as in the use of the aluminum compound (1) are yielded. This is considered to be attributable to the fact that an aluminum compound (1) is formed by the reaction of (A) the aluminum alkoxide with (B) the phenol and/or the sulfonic acid, and this aluminum compound functions as an acid catalyst.

More specifically, the alcohols is reacted with the carbonyl compound, alcohol, olefin, epoxy compound or sugar in the presence of (A) the aluminum alkoxide and (B) the phenol and/or the sulfonic acid, thereby obtaining an ester, acetal, ketal, ether or alkyl glycoside at a high yield.

The aluminum alkoxide used in this reaction may be any of mono-, di- and trialkoxides, with the trialkoxides being preferred. The number of carbon atoms in the alkoxyl group is preferably 1 to 4. Specific examples of the aluminum trialkoxide include aluminum trimethoxide, aluminum triethoxide, aluminum triisopropoxide and aluminum tributoxide, with aluminum triisopropoxide being particularly preferred. With respect to these compounds, marketed products may be used. However, a mixture of mono- , di- and trialkoxides, which is obtained by reacting an aluminum trihalide or trialkylaluminum with an alcohol, may also be used. In this case, it is preferred to select such conditions that the resulting mixture will contain the trialkoxide in a greater amount.

(B) The phenol may be any compound which may be substituted by at least one halogen atom so far as it has a phenolic hydroxyl group. Examples thereof include phenol, chlorophenol, dichlorophenol, 2,4,6-trichlorophenol, 1-naphthol, 2-naphthol, hydroquinone, 2,2-bis(4-hydroxyphenyl)propane, bis(4-hydroxyphenyl) sulfone and binaphthol.

Examples of (B) the sulfonic acid include those in which $R^1$ is an alkyl or alkenyl group which may be substituted by at least one hydroxyl group, alkoxyl group or halogen atom; or an aryl group which may be substituted by at least one alkyl group, hydroxyl group, alkoxyl group or halogen atom. These alkyl group and the like are the same at those described above. Specific examples of the sulfonic acid include methanesulfonic acid, trichloromethanesulfonic acid, and benzenesulfonic acid or napthalenesulfonic acid which may be substituted by an alkyl group having 1 to 12 carbon atoms or a hydroxyl group. Preferable examples thereof include 2,4,6-trichlorophenol, methanesulfonic acid, p-toluenesulfonic acid, phenolsulfonic acid, dodecylbenzenesulfonic acid and naphthalenesulfonic acid, with phenolsulfonic acid being particularly preferred.

Of these, a combination of aluminum triisopropoxide as (A) and p-phenolsulfonic acid as (B) is most preferred.

Even when the reaction is performed in the presence of (A) the aluminum alkoxide and (B) the phenol and/or the sulfonic acid as described above, the proportions of the starting materials used, reaction temperature and reaction time are the same as in the reaction making use of the aluminum compound (1). With respect to the amounts of (A) the aluminum alkoxide and (B) the phenol and/or the sulfonic acid used, for example, in the reaction of the alcohol with the epoxy compound, it is preferable to use (A) the aluminum alkoxide in an amount of 0.001 to 0.1 mol, particularly 0.01 to 0.05 mol per mol of the alcohol, and (B) the phenol and/or the sulfonic acid in an amount of 1.0 to 3.0 mol, particularly 2.0 to 3.0 mol per mol of the aluminum alkoxide. In the reaction of the alcohol with the sugar, it is preferable to use (A) the aluminum alkoxide in an amount of 0.001 to 0.1 mol, particularly 0.001 to 0.01 mol per mol of the sugar, and (B) the phenol and/or the sulfonic acid in an amount of 1.0 to 3.0 mol, particularly 2.0 to 3.0 mol per mol of the aluminum alkoxide.

The esters, acetals, ketals, ethers or glycidyl ethers obtained in the above-described manner may be isolated and purified by any known isolation and purification means, specifically, distillation, recrystallization, column chromatography and/or the like.

EXAMPLES

The present invention will hereinafter be described in more detail by the following examples. However, the present invention is not limited to these examples.

Example 1

Toluene (50 ml), aluminum triisopropoxide (3.60 g; 17.6 mmol) and p-phenolsulfonic acid (9.21 g; 52.8 mmol) were placed in a 100-ml four-necked flask, and refluxed by means of a Dean-Stark trap for 3 hours while stirring them under nitrogen. The solvent was distilled off to obtain 9.6 g of a compound (a) according to the present invention as a pale yellowish-white solid. [m.p.=300° C. (decomp.)]. This compound was identified by solid FT-IR as illustrated in FIG. 1.

$V_{OH}$=3281 cm$^{-1}$ (phenolic hydroxyl group) (disappearance of C—H stretching, $V_{C-H}$=2800–3000 cm$^{-1}$, derived from the isopropyl group of aluminum triisopropoxide)

Octyl alcohol (11.7 g; 0.09 mol) and the compound (a) (0.98 g; 1.80 mmol) according to the present invention were placed in a 100-ml four-necked flask and heated up to 95° C. while stirring them under nitrogen. Epichlorohydrin (10.0 g; 0.108 mol) was then added dropwise over 10 minutes, and the resultant mixture was stirred for 3 hours as it was. The yield of a halohydrin ether formed was determined by GLC and found to be 87%. The remaining amount of unreacted octyl alcohol was also determined by GLC and found to be 5% or less.

Example 2

Octyl alcohol (11.7 g; 0.09 mol), aluminum triisopropxide (0.36 g; 1.77 mmol) and p-phenolsulfonic acid (0.94 g; 5.40 mmol) were placed in a 100-ml four-necked flask and heated up to 95° C. while stirring them under nitrogen. Epichlorohydrin (10.0 g; 0.108 mol) was then added dropwise over 10 minutes, and the resultant mixture was stirred for 3 hours as it was. The yield of a halohydrin ether formed was determined by GLC and found to be 87%. The remaining amount of unreacted octyl alcohol was also determined by GLC and found to be 5% or less.

A 4N aqueous solution (40 ml) of sodium hydroxide was added to this reaction mixture, and the resultant mixture was stirred at 85 to 90° C. for 3 hours. After the reaction mixture was cooled down to room temperature, a water layer was removed, and the residue was washed twice with water (30 ml) and purified by vacuum distillation to obtain 14.2 g of octyl glycidyl ether (1,2-epoxy-4-oxadodecane) as a colorless transparent oil (total yield: 85%).

$^1$H-NMR (200 MHz, CDCl$_3$): δ ppm 0.9(3H, triplet, 12-position methyl), 1.2–1.5(10H, overlapped broad peak, 7- to 11-position methylene), 1.51(2H, triplet, 6-position methylene) 2.65, 2.8(2H, each quartet, 1-position methylene), 3.18(1H, multiplet, 2-position methyne), 3.38 and 3.7, 3.45 and 3.76(2H, each doublet, 3-position methylene) 3.5(2H, broad multiplet, 5-position methylene).

Purity (GLC): 99.5%.

Comparative Example 1

Octyl alcohol (11.7 g; 0.09 mol) and aluminum triisopropxide (0.36 g; 1.77 mmol) were placed in a 100-ml four-necked flask and heated up to 95° C. while stirring them under nitrogen. Epichlorohydrin (10.0 g; 0.108 mol) was then added dropwise over 10 minutes, and the resultant mixture was stirred for 3 hours as it was. The yield of a halohydrin ether formed was 6%, and the remaining amounts of unreacted octyl alcohol and epichlorohydrin were both 90% or more.

Comparative Example 2

Octyl alcohol (11.7 g; 0.09 mol) and p-phenylsulfonic acid (0.94 g) were placed in a 100-ml four-necked flask and heated up to 95° C. while stirring them under nitrogen. Epichlorohydrin (10.0 g; 0.108 mol) was then added dropwise over 10 minutes, and the resultant mixture was stirred for 3 hours as it was. The yield of a halohydrin ether formed was 22%, and the remaining amount of unreacted octyl alcohol was 65% or more.

Comparative Example 3

Octyl alcohol (11.7 g; 0.09 mol) and BF$_3$(OEt$_2$) (0.25 g; 1.77 mmol) were placed in a 100-ml four-necked flask and epichlorohydrin (10.0 g; 0.108 mol) was added dropwise over 30 minutes while stirring them under nitrogen. The resultant mixture was stirred for 3 hours as it was. Epichlorohydrin was completely consumed, but the yield of a halohydrin ether formed was 61%.

Example 3

Octyl alcohol (11.7 g; 0.09 mol), aluminum triisopropxide (0.36 g; 1.77 mmol) and p-phenolsulfonic acid (0.94 g; 5.40 mmol) were placed in a 100-ml four-necked flask and heated up to 95° C. while stirring them under nitrogen. Octyl glycidyl ether (17.1 g; 0.09 mol) was then added dropwise over 10 minutes, and the resultant mixture was stirred for 3 hours as it was. After completion of the reaction, the reaction mixture was washed with a 4N aqueous solution (40 ml) of sodium hydroxide and additionally twice with water (40 ml) and then purified by vacuum distillation to obtain 23.0 g of 1,3-dioctyl glyceryl ether (9,13-dioxa-11-heneicosanol) as a colorless transparent oil (yield: 81%).

$^1$H-NMR (200 MHz, CDCl$_3$): δ ppm 0.88(6H, triplet, 1- and 21-position methyl), 1.2–1.5(20H, overlapped broad peak, 2- to 6- and 16- to 20-position methylene), 1.58(4H, triplet, 7- and 15-position methylene) 2.7(1H, doublet, hydroxyl group), 3.46(8H, overlapped triplet and doublet, 8-, 10-, 14- and 21-position methylene), 3.96(1H, multiplet, 11-position methyne).

Purity (GLC): 95.0% (content of 1,2-dioctyl glyceryl ether: 5%).

Comparative Example 4

Octyl alcohol (11.7 g; 0.09 mol) and methanesulfonic acid (0.50 g; 5.50 mmol) were placed in a 100-ml four-necked flask and heated up to 95° C. while stirring them under nitrogen. Octyl glycidyl ether (17.1 g; 0.09 mol) was then added dropwise over 10 minutes, and the resultant mixture was stirred for 8 hours as it was. After completion of the reaction, the reaction mixture was washed with a 4N aqueous solution (40 ml) of sodium hydroxide and additionally twice with water (40 ml) and then purified by column chromatography on silica gel (developing solvent: hexane) to obtain 2.0 g of 1,3-dioctyl glyceryl ether (9,13-dioxa-11-heneicosanol) as a colorless transparent oil (yield: 7%).

Comparative Example 5

A reaction was performed in the same manner as in Example 3 except that no aluminum triisopropoxide was used. As a result, the yield of the glyceryl ether was 3%.

Comparative Example 6

A reaction was performed in the same manner as in Example 3 except that no p-phenolsulfonic acid was used. As a result, the yield of the glyceryl ether was 15%.

Example 4

Hexadecyl alcohol (21.8 g; 0.09 mol) and the compound (a) (1.00 g; 1.83 mmol) according to the present invention were placed in a 100-ml four-necked flask and heated up to 80° C. while stirring them under nitrogen. Butyl glycidyl ether (11.7 g; 0.09 mol) was then added dropwise over 10 minutes, and the resultant mixture was stirred for 4 hours as it was. After completion of the reaction, the reaction mixture was washed with a 4N aqueous solution (40 ml) of sodium hydroxide and additionally twice with water (40 ml) and then purified by vacuum distillation to obtain 26.8 g of 1-butyl-3-hexadecyl glyceryl ether as a colorless transparent oil (total yield: 80%). The compound was identified by $^1$H-NMR (200 MHz). The purity of the compound was found to be 95.0% by GLC, and 5% of 1-butyl-2-hexadecyl glycidyl ether was contained therein.

Example 5

Hexadecyl alcohol (21.8 g; 0.09 mol), aluminum triisopropxide (0.36 g; 1.77 mmol) and 2,4,6-trichlorophenol (0.76 g; 5.29 mmol) were placed in a 100-ml four-necked flask and heated up to 80° C. while stirring them under nitrogen. Butyl glycidyl ether (11.7 g; 0.09 mol) was then added dropwise over 10 minutes, and the resultant mixture was stirred for 4 hours as it was. After completion of the reaction, the reaction mixture was washed with a 4N aqueous solution (40 ml) of sodium hydroxide and additionally twice with water (40 ml) and then purified by vacuum distillation to obtain 26.8 g of 1-butyl-3-hexadecyl glyceryl ether as a colorless transparent oil (total yield: 80%). The compound was identified by $^1$H-NMR (200 MHz). The purity of the compound was found to be 95.0% by GLC, and 5% of 1-butyl-2-hexadecyl glycidyl ether was contained therein.

Example 6

Hexadecyl alcohol (21.8 g; 0.09 mol) was placed in a 100-ml four-necked flask and heated up to 70° C. Aluminum triisopropxide (0.36 g; 1.77 mmol) and p-phenolsulfonic acid (0.94 g; 5.40 mmol) were added, and the resultant mixture was heated up to 100° C. while stirring it under nitrogen. Epichlorohydrin (10.0 g; 0.108 mol) was then added dropwise over 10 minutes, and the resultant mixture was stirred for 3 hours as it was. The yield of a halohydrin ether formed was determined by GLC and found to be 85%. The remaining amount of unreacted octyl alcohol was 5% or less.

A 4N aqueous solution (40 ml) of sodium hydroxide was added to this reaction mixture, and the resultant mixture was stirred at 85 to 90° C. for 3 hours. After hexane (50 ml) was added, and the mixture was cooled down to room temperature, a water layer was removed, and the residue was washed twice with water (30 ml). The solvent was distilled off, and the residue was purified by column chromatography on silica gel to obtain 22.3 g of hexadecyl glycidyl ether (1,2-epoxy-4-oxaeicosane) as white crystals (total yield: 85%). The compound was identified by $^1$H-NMR (200 MHz). The purity of the compound was found to be 99% by GLC.

Example 7

Octyl alcohol (11.7 g; 0.09 mol), aluminum triisopropxide (0.36 g; 1.77 mmol) and 1-naphthol (0.76 g; 5.29 mmol) were placed in a 100-ml four-necked flask and heated up to 95° C. while stirring them under nitrogen. Epichlorohydrin (10.0 g; 0.108 mol) was then added dropwise over 10 minutes, and the resultant mixture was stirred for 3 hours as it was. The yield of a halohydrin ether formed was determined by GLC and found to be 88%. The remaining amount of unreacted octyl alcohol was 4% or less.

Example 8

Octyl alcohol (11.7 g; 0.09 mol), aluminum triisopropxide (0.36 g; 1.77 mmol) and 2,4,6-trichlorophenol (1.04 g; 5.29 mmol) were placed in a 100-ml four-necked flask and heated up to 90° C. while stirring them under nitrogen. Epichlorohydrin (10.0 g; 0.108 mol) was then added dropwise over 10 minutes, and the resultant mixture was stirred for 2 hours as it was. The yield of a halohydrin ether formed was determined by GLC and found to be 87%. The remaining amount of unreacted octyl alcohol was 3% or less.

Example 9

Octyl alcohol (117 g; 0.900 mol), aluminum triisopropxide (3.61 g; 17.7 mmol) and p-phenolsulfonic acid (9.40 g; 5.401 mol) were placed in a 1-l eggplant type flask and heated up to 100° C. while stirring them. After the mixture was further stirred for 1 hour under reduced pressure, epichlorohydrin (100 g) was added dropwise over 30 minutes, and the resultant mixture was stirred for 3 hours as it was. The yield of a halohydrin ether formed was determined by GLC and found to be 87%. The reaction mixture was kept at 50° C., and a 48% aqueous solution (400 ml) of sodium hydroxide was added dropwise over 1 hour, and the resultant mixture was stirred for 3 hours as it was. Water (200 ml) was then added to conduct phase separation. A water layer was removed, and the residue was washed twice with water (300 ml) to obtain 200 g of crude octyl glycidyl ether.

The crude octyl glycidyl ether (175 g), water (110 g; 6.111 mol), lauric acid (7.10 g; 0.033 mol) and sodium hydroxide (0.71 g; 0.018 mol) were placed in a 2-l autoclave, and the mixture was heated up to 157° C. while stirring it. The mixture was stirred for 5 hours as it was, and was then allowed to cool down to room temperature. The mixture was extracted with ethyl acetate (500 ml), and the extract was washed twice with water (300 ml). The solvent was then distilled off to obtain 165 g of crude monooctyl glyceryl ether. This crude product was purified by vacuum distillation (0.4–0.5 mmHg, 120–123° C.) to obtain 124 g of monooctyl glyceryl ether as a colorless transparent oil (total yield: 75%). Quenching of a proton signal (methylene in an epoxy ring) at δ=2.65, 2.80 was observed by $^1$H-NMR (200 MHz), thereby identifying the compound. The purity of the compound was found to be 99% by GLC.

Example 10

Isoamyl alcohol (158 g; 1.78 mol), aluminum triisopropxide (3.61 g; 17.7 mmol) and p-phenolsulfonic acid (9.40 g; 5.401 mol) were placed in a 1-l eggplant type flask and heated up to 90° C. while stirring them. After the mixture was further stirred for 1 hour under reduced pressure, it was heated up to 100° C., and epichlorohydrin (170 g) was added dropwise over 30 minutes. The resultant mixture was stirred for 3 hours as it was. The yield of a halohydrin ether formed was determined by GLC and found to be 86%. The reaction mixture was kept at 50° C., and a 48% aqueous solution (800 ml) of sodium hydroxide was added dropwise over 1 hour, and the resultant mixture was stirred for 3 hours as it was. Water (400 ml) was then added to conduct phase separation. A water layer was removed, and the residue was washed twice with water (500 ml) to obtain 280 g of crude isoamyl glycidyl ether.

The crude isoamyl glycidyl ether (140 g), water (140 g; 7.78 mol), lauric acid (7.64 g; 0.038 mol) and potassium hydroxide (2.14 g; 0.038 mol) were placed in a 2-l autoclave, and the mixture was heated up to 157° C. while stirring it. The mixture was stirred for 5 hours as it was, and was then allowed to cool down to room temperature. The mixture was extracted with ethyl acetate (500 ml), and the extract was washed twice with water (300 ml). The solvent was then distilled off to obtain 157 g of crude monoisoamyl glyceryl ether. This crude product was purified by vacuum distillation (2 mmHg, 114–115° C.) to obtain 103 g of monoisoamyl glyceryl ether as a colorless transparent oil (total yield: 71%). Quenching of a proton signal (methylene in an epoxy ring) at δ=2.60, 2.80 was observed by $^1$H-NMR (200 MHz), thereby identifying the compound. The purity of the compound was found to be at least 99% by GLC.

Example 11

Octyl alcohol (11.7 g; 0.09 mol) and the compound (a) (1.00 g; 1.83 mmol) according to the present invention were placed in a 100-ml four-necked flask and heated up to 100° C. while stirring them under nitrogen. 1,2-Epoxydecane (16.6 g; 0.09 mol) was then added, and the resultant mixture was stirred for 3 hours as it was. After completion of the reaction, the reaction mixture was washed with a 4N aqueous solution (40 ml) of sodium hydroxide and additionally twice with water (40 ml) and then purified by vacuum distillation to obtain 21.3 g of 11-oxa-9-hydroxynonadecane as a colorless transparent oil (total yield: 83%). The compound was identified by $^1$H-NMR (200 MHz). The purity of the compound was found to be 95.0% by GLC, and 5% of 10-oxa-9-hydroxymethylnonadecane was contained therein.

Example 12

Octyl alcohol (11.7 g; 0.09 mol), aluminum triisopropxide (0.36 g; 1.77 mmol) and p-phenolsulfonic acid (0.94 g; 5.40 mmol) were placed in a 100-ml four-necked flask and heated up to 100° C. while stirring them under nitrogen. 1,2-Epoxydecane (16.6 g; 0.09 mol) was then added, and the resultant mixture was stirred for 3 hours as it was. After completion of the reaction, the reaction mixture was washed with a 4N aqueous solution (40 ml) of sodium hydroxide and additionally twice with water (40 ml) and then purified by vacuum distillation to obtain 21.3 g of 11-oxa-9-hydroxynonadecane as a colorless transparent oil (total yield: 83%). The compound was identified by $^1$H-NMR (200 MHz). The purity of the compound was found to be 95.0% by GLC, and 5% of 10-oxa-9-hydroxymethylnonadecane was contained therein.

Example 13

Decyl alcohol (539.0 g; 3.41 mol) and anhydrous glucose (245 g; 1.36 mol) were placed in a 2-l four-necked flask and heated up to 100° C. while keeping them at a pressure of 35 to 40 mmHg under nitrogen and stirring them. The compound (a) (2.0 g) according to the present invention was added, and the resultant mixture was stirred for 9 hours as it was. As a result, the conversion of glucose reached 97%. After completion of the reaction, the reaction mixture was dispersed in hexane (2 l), and a trace amount of unreacted glucose was then removed from the reaction mixture by filtration. The residue was neutralized to pH 6.7 with a 2N aqueous solution of sodium hydroxide. Hexane and decyl alcohol were distilled off to obtain 371 g of decyl glycoside. The remaining amount of unreacted decyl alcohol was found to be 1.2% by gas chromatography. By $^1$H-NMR (200 MHz; CDCl$_3$/D$_2$O solvent), the formed decyl glycoside was also found to have a glucose skeleton in which glucose was condensed in a proportion of 1.28 mol in average per mol of the glycoside (condensation degree: 1.28).

Example 14

Decyl alcohol (50.20 g; 0.381 mol), aluminum triisopropxide (15.68 g; 0.077 mol) and p-phenolsulfonic acid (40.12 g; 0.231 mol) were placed in a 200-ml eggplant type flask and heated up to 100° C. while stirring them. The mixture was further stirred for 3 hours under reduced pressure (50 mmHg) and then diluted with decyl alcohol (111 g) to prepare a 20% catalyst solution (210 g).

Decyl alcohol (539.0 g; 3.41 mol) and anhydrous glucose (245 g; 1.36 mol) were placed in a 2-l four-necked flask and heated up to 100° C. while keeping them at a pressure of 35 to 40 mmHg under nitrogen and stirring them. The 20% catalyst solution (10 g) prepared previously was added dropwise, and the resultant mixture was stirred for 9 hours as it was. As a result, the conversion of glucose reached 97%. After completion of the reaction, the reaction mixture was dispersed in hexane (2 l), and a trace amount of unreacted glucose was then removed from the reaction mixture by filtration. The residue was neutralized to pH 6.7 with a 2N aqueous solution of sodium hydroxide. Hexane and decyl alcohol were distilled off to obtain 370 g of decyl glycoside. The remaining amount of unreacted decyl alcohol was found to be 1.3% by gas chromatography. By $^1$H-NMR (200 MHz; CDCl$_3$/D$_2$O solvent), the formed decyl glycoside was also found to have a glucose skeleton in which glucose was condensed in a proportion of 1.30 mol in average per mol of the glycoside (condensation degree: 1.30).

Comparative Example 7

Decyl alcohol (539.0 g; 3.41 mol) and anhydrous glucose (245 g; 1.36 mol) were placed in a 2-l four-necked flask and heated up to 100° C. while keeping them at a pressure of 35 to 40 mmHg under nitrogen and stirring them. p-Toluenesulfonic acid (1.0 g) was added, and the resultant mixture was stirred for 6 hours as it was. As a result, the conversion of glucose reached 98%. After completion of the reaction, the reaction mixture was dispersed in hexane (2 l), and a trace amount of unreacted glucose was then removed from the reaction mixture by filtration. The residue was neutralized to pH 6.7 with a 2N aqueous solution of sodium hydroxide. Hexane and decyl alcohol were distilled off to obtain 270 g of decyl glycoside. The remaining amount of unreacted decyl alcohol was found to be 1.3% by gas chromatography. By $^1$H-NMR (200 MHz; CDCl$_3$/D$_2$O solvent), the formed decyl glycoside was also found to have a glucose skeleton in which glucose was condensed in a proportion of 2.40 mol in average per mol of the glycoside (condensation degree: 2.40).

Example 15

Dodecyl alcohol (50.20 g; 0.318 mol), aluminum triisopropxide (15.68 g; 0.077 mol) and p-phenolsulfonic acid (40.12 g; 0.231 mol) were placed in a 200-ml eggplant type flask and heated up to 100° C. while stirring them. The mixture was further stirred for 3 hours under reduced pressure (50 mmHg) and then diluted with dodecyl alcohol (111 g) to prepare a 20% catalyst solution (210 g).

Dodecyl alcohol (4.5.0 g; 2.72 mol) and anhydrous glucose (245 g; 1.36 mol) were placed in a 2-l four-necked. flask and heated up to 100° C. while keeping them at a pressure of 35 to 40 mmHg under nitrogen and stirring there. The 20% catalyst solution (10 g) prepared previously was added dropwise, and the resultant mixture was stirred for 9 hours as it was. As a result, the conversion of glucose reached 95%. After completion of the reaction, the reaction mixture was dispersed in hexane (2 l), and a trace amount of unreacted glucose was then removed from the reaction mixture by filtration. The residue was neutralized to pH 6.5 with a 2N aqueous solution of sodium hydroxide. Hexane and decyl alcohol were distilled off to obtain 385 g of dodecyl glycoside. The remaining amount of unreacted dodecyl alcohol was found to be 1.5% by gas chromatography. By $^1$H-NMR (200 MHz; CDCl$_3$/D$_2$O solvent), the formed decyl glycoside was also found to have a glucose skeleton in which glucose was condensed in a proportion of 1.28 mol in average per mol of the glycoside (condensation degree; 1.28).

From the above, it was confirmed that the condensation of sugar was inhibited in Examples 13 to 15 compared with Comparative Example 7, and so the yield of the alkyl glycoside was enhanced.

Example 16

Toluene (50 ml), aluminum triisopropoxide (5.00 g; 24.5 mmol), phenol (2.35 g; 24.6 mmol) and methanesulfonic acid (4.71 g; 49.1 mmol) were placed in a 100-ml four-necked flask and stirred at 90° C. for 3 hours. The solvent was distilled off to obtain 7.6 g of a compound (j) according to the present invention as a white solid. Quenching of a phenolic hydroxyl group was observed by solid FT-IR, thereby identifying the compound.

Octyl alcohol (11.7 g; 0.09 mol) and the compound (j) (0.31 g; 1.0 mmol) according to the present invention were placed in a 100-ml four-necked flask and heated up to 95° C. while stirring them under nitrogen. Epichlorohydrin (10.0 g; 0.108 mol) was then added dropwise over 10 minutes, and the resultant mixture was stirred for 5 hours as it was. The yield of a halohydrin ether formed was determined by GLC and found to be 86%. The remaining amount of unreacted octyl alcohol was also determined by GLC and found to be 5% or less.

INDUSTRIAL APPLICABILITY

The aluminum compounds (1) are not deactivated by alcoholysis and high in catalytic activity and are hence useful as acid catalysts for a variety of reactions using alcohols as starting materials.

What is claimed is:

1. An aluminum compound represented by the following general formula (1):

wherein $R^1$ is a hydrocarbon group which may be substituted (except a halogenated alkyl group), $R^2$ is an alkyl, alkenyl, alkoxyl or alkenyloxy group which may be substituted by at least one hydroxyl group, alkoxyl group, polyoxyalkylene group, or a halogen atom, $R^3$ is an aromatic hydrocarbonoxy group which may be substituted,, 1 is a number of 1 to 3, m is a number of 1 to 2, and n is a number of 0 to 1, with the proviso that l+m+n equals 3.

2. The aluminum compound according to claim 1, wherein in the general formula (1), $R^1$ is an alkyl or alkenyl group which may be substituted by at least one hydroxyl group or alkoxyl group, or an aryl group which may be substituted by at least one alkyl group, hydroxyl group, alkoxyl group or halogen atom, and $R^3$ is an aryloxy group which may be substituted by at least one alkyl group, hydroxyl group, alkoxyl group or halogen atom.

3. The aluminum compound according to any one of claims 1 to 2, wherein in the general formula (1), $R^2$ is an isopropoxyl group.

4. An acid catalyst comprising the aluminum compound according to any one of claims 1 to 3.

5. A process for producing an ester, acetal, ketal, ether or alkyl glycoside, which comprises reacting an alcohol with a carbonyl compound, alcohol, olefin, epoxy compound or sugar in the presence of an acid catalyst of an aluminum compound represented by the following general formula (1):

wherein $R^1$ is a hydrocarbon group which may be substituted (except a halogenated alkyl group), $R^2$ is a hydrocarbon group which may be substituted, an aliphatic hydrocarbonoxy group which may be substituted or a halogen atom, $R^3$ is an aromatic hydrocarbonoxy group which may be substituted, and l, m and n are independently a number of 0 to 3, with the proviso that l+m+n equals 3, and l is not 0.

6. A process for producing an ether, which comprises reacting an alcohol with an epoxy compound in the presence of the acid catalyst according to claim 4.

7. The production process of the ether according to claim 6, wherein the epoxy compound is an epihalohydrin.

8. A process for producing an alkyl glycoside, which comprises reacting an alcohol with a sugar in the presence of the acid catalyst according to claim 4.

9. A process for producing an ester, acetal, ketal, ether or alkyl glycoside, which comprises reacting an alcohol with a carbonyl compound, alcohol, olefin, epoxy compound (except a vicinal alkylene oxide having 2 to 4 carbon atoms) or sugar in the presence of (A) an aluminum alkoxide and (B) a phenol and/or a sulfonic acid.

10. The production process of the ether according to claim 9, wherein (B) the phenol and/or the sulfonic acid is phenol or naphthol which may be substituted by at least one halogen atom, or a benzenesulfonic acid or naphthalenesulfonic acid which may be substituted by an alkyl group having 1 to 12 carbon atoms, or a hydroxyl group.

11. A process for producing an ether, which comprises reacting an alcohol with an epoxy compound in the presence of (A) an aluminum alkoxide and (B) a phenol and/or a sulfonic acid.

12. The production process of the ether according to claim 11, wherein the epoxy compound is an epihalohydrin.

13. A process for producing a glycidyl ether, which comprises reacting the ether obtained in claim 12 with an alkali.

14. A process for producing a monoalkyl glyceryl ether, which comprises hydrolyzing the glycidyl ether obtained in claim 13.

* * * * *

UNITED STATES PATENT AND TRADEMARK OFFICE
CERTIFICATE OF CORRECTION

PATENT NO. : 6,207,845 B1
DATED : March 27, 2001
INVENTOR(S) : Muneshisa Okutsu, et al.

It is certified that error appears in the above-identified patent and that said Letters Patent is hereby corrected as shown below:

Item [30], Foreign Application Priority Data
May 1, 1997   (JP) ..................................................... 9-113855
Sep. 12, 1997  (JP) ..................................................... 9-248156 --

Signed and Sealed this

Twenty-third Day of October, 2001

Attest:

NICHOLAS P. GODICI
Attesting Officer    Acting Director of the United States Patent and Trademark Office